United States Patent
Fossum (10) Patent No.: US 12,187,934 B2
(45) Date of Patent: Jan. 7, 2025

(54) THERMALLY ACTIVATED DELAYED FLUORESCENCE CHROMOPHORES AND ORGANIC LAYERS INCLUDING THE SAME

(71) Applicant: Wright State University, Dayton, OH (US)

(72) Inventor: Eric Fossum, Middletown, OH (US)

(73) Assignee: Wright State University, Dayton, OH (US)

( * ) Notice: Subject to any disclaimer, the term of this patent is extended or adjusted under 35 U.S.C. 154(b) by 859 days.

(21) Appl. No.: 16/668,876

(22) Filed: Oct. 30, 2019

(65) Prior Publication Data
US 2020/0131436 A1 Apr. 30, 2020

Related U.S. Application Data

(60) Provisional application No. 62/753,297, filed on Oct. 31, 2018.

(51) Int. Cl.
| C07D 277/66 | (2006.01) |
| C08G 65/40 | (2006.01) |
| C09K 11/06 | (2006.01) |

(52) U.S. Cl.
CPC ............ C09K 11/06 (2013.01); C07D 277/66 (2013.01); C08G 65/40 (2013.01); C09K 2211/1018 (2013.01)

(58) Field of Classification Search
CPC ......... C08G 65/40; C08G 75/23; C08L 81/06; C09K 11/06; C09K 2211/1018; C07D 277/66
See application file for complete search history.

(56) References Cited

FOREIGN PATENT DOCUMENTS

| CN | 103483332 | * | 1/2014 |
| CN | 107118334 | * | 9/2017 |
| CN | 108239070 | * | 7/2018 |
| JP | 2013-216630 | * | 10/2013 |
| KR | 2014-0127701 | * | 11/2014 |

OTHER PUBLICATIONS

Xu et al. (Chemical Science (2016), 7(3), 2201-2206).*
Picker, J. L. (2014). Routes to N-Heterocycle Functionalized Poly(arylene ether sulfone)s [Master's thesis, Wright State University]. OhioLINK Electronic Theses and Dissertations Center. http://rave.ohiolink.edu/etdc/view?acc_num=wright1409597075.*
Kemboi, Abraham K. "Design and Application of Facile Routes to N-Heterocycle Functionalized Poly(arylene ether)s" (2016) [Master's thesis, Wright State University]. OhioLINK Electronic Theses and Dissertations Center.*
Konidena (ACS Appl. Mater. Interfaces 2018, 10, 24013-24027).*
Sallenave (J. Phys. Chem. C 2018, 122, 10138-10152).*

* cited by examiner

*Primary Examiner* — Valerie Rodriguez-Garcia (57) ABSTRACT

A thermally activated delayed fluorescence chromophore of the general structure:

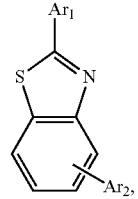

wherein $Ar_1$ represents an acceptor tuner ligand and $Ar_2$ represents a donor ligand, wherein the acceptor tuner ligand is a benzene ring at least partially substituted with two or more fluoro atoms and wherein the donor ligand is an optionally substituted carbazole. Organic layers, such as polymers or films, comprising the thermally activated delayed fluorescence chromophores are also disclosed.

4 Claims, 4 Drawing Sheets

THERMALLY ACTIVATED DELAYED FLUORESCENCE CHROMOPHORES AND ORGANIC LAYERS INCLUDING THE SAME

CROSS-REFERENCE TO RELATED APPLICATION

This application claims priority to U.S. Provisional Application Ser. No. 62/753,297, filed Oct. 31, 2018, which is hereby incorporated by reference in its entirety.

This invention was made with government support under CHE1307117 awarded by National Science Foundation. The government has certain rights in the invention.

BACKGROUND

Field

The present disclosure relates to chromophores and, more specifically, to thermally activated delayed fluorescence chromophores and organic layers comprising the same.

Technical Background

Chromophores, which are molecules, or regions of molecules, responsible for the color of a material due to the emission of visible light, are widely used in organic light emitting diodes (OLEDs). Organic light emitting diodes have significant utility in both the scientific community and display industry, such as in the digital displays of monitors, mobile devices, and televisions. However, organic light emitting diodes may often have poor efficiency and require rare and costly material for production. In particular, blue-emitting diodes typically achieve a maximum external quantum efficiency of only 4 percent (%) to 6%, while red-emitting diodes and green-emitting diodes typically achieve maximum external quantum efficiencies of 20% and 19%, respectively. Accordingly, organic light emitting diodes incorporating chromophores that undergo a process termed thermally activated delayed fluorescence (TADF) have been developed. Chromophores capable of undergoing the thermally activated delayed fluorescence process have shown the capacity to greatly enhance the efficiency of organic light emitting diodes without the need for rare and costly materials. In particular, blue-emitting diodes that incorporate chromophores capable of undergoing the thermally activated delayed fluorescence process have achieved significant increases in external quantum efficiency compared to conventional blue-emitting organic light emitting diodes.

However, despite these potentially advantageous properties, chromophores capable of undergoing the thermally activated delayed fluorescence process typically lack other properties that may make them suitable for use in practical applications. For example, conventional chromophores capable of undergoing the thermally activated delayed fluorescence process typically lack the thermo-oxidative stability necessary for extended operating conditions. As a result, the long-term stability of organic light emitting diodes that incorporate chromophores capable of undergoing the thermally activated delayed fluorescence process may be negatively affected. Moreover, conventional chromophores capable of undergoing the thermally activated delayed fluorescence process typically lack a means to be efficiently tailored to a desired emission profile. Moreover, conventional chromophores capable of undergoing the thermally activated delayed fluorescence process typically lack a means to be readily incorporated into an organic layer, such as a polymer matrix or film, which may be required for some practical applications.

SUMMARY

Accordingly, there is an ongoing need for thermally activated delayed fluorescence chromophores that have improved thermo-oxidative stability, that may be efficiently tailored, and that may be readily incorporated into an organic layer. The chromophores of the present disclosure are capable of undergoing the thermally activated delayed fluorescence process and generally comprise at least a π-donor ligand, a π-acceptor ligand, and an acceptor tuner ligand. The chromophores of the present disclosure may have excellent thermo-oxidative stability when compared to conventional chromophores capable of undergoing the thermally activated delayed fluorescence process. Moreover, this modular approach that utilizes three ligands may allow for the efficient tailoring of the chromophores to a desired emission profile with simple structural modifications. Furthermore, the molecular structures may allow the chromophores to be readily incorporated into organic layers, such as a polymer matrix, which may further improve the processing and long-term stability of the chromophores when incorporated into practical applications.

According to one or more embodiments of the present disclosure, a thermally activated delayed fluorescence chromophore may comprise a donor ligand, an acceptor ligand, and an acceptor tuner ligand. The donor ligand may be selected from one or more of carbazole, diphenylamine, phenothiazine, phenoxazine, or acridine. The acceptor ligand may be selected from one or more of benzoxazole, benzothiazole, or diphenyl sulfone. The acceptor tuner ligand may comprise a benzene ring. The benzene ring may be at least partially substituted.

According to one or more additional embodiments of the present disclosure, a poly(arylene ether) may comprise a thermally activated delayed fluorescence chromophore and at least one monomer. The thermally activated delayed fluorescence chromophore may comprise a donor ligand, an acceptor ligand, and an acceptor tuner ligand. The donor ligand may be selected from one or more of carbazole, diphenylamine, phenothiazine, phenoxazine, or acridine. The acceptor ligand may be selected from one or more of benzoxazole, benzothiazole, or diphenyl sulfone. The acceptor tuner ligand may comprise a benzene ring. The benzene ring may be at least partially substituted. The monomer may be selected from one or more of 4,4'-difluorodiphenyl sulfone, 4,4'-difluorobenzophenone, 4,4'-difluorotriphenylphosphine oxide, 2,5-bis(4-fluorophenyl)-1,3,4-oxadiazole, 2,3-bis(4-fluorophenyl)-quinoxaline, 2,5-bis(4-fluorophenyl)-oxazole, bisphenol-A, bisphenol-AF, 4,4'-dihydroxybiphenyl, 4,4'-dihydroxydiphenyl ether, hydroquinone, catchol, or resorcinol.

Additional features and advantages of the technology described in the present disclosure will be set forth in the detailed description that follows, and in part will be readily apparent to those skilled in the art from the description or recognized by practicing the technology as described in this disclosure, including the detailed description that follows, as well as the claims.

BRIEF DESCRIPTION OF THE DRAWINGS

The following detailed description of embodiments of the present disclosure can be best understood when read in conjunction with the following drawings in which.

Reference will now be made in greater detail to various embodiments, some embodiments of which are illustrated in the accompanying drawings.

DETAILED DESCRIPTION

The present disclosure is directed to thermally activated delayed fluorescence chromophores and organic layers comprising the same. The chromophores of the present disclosure may generally comprise a donor ligand, an acceptor ligand, and an acceptor tuner ligand. The structure of these chromophores may allow the chromophores to undergo thermally activated delayed fluorescence. That is, these chromophores may be capable of transitioning from a triplet state to a singlet state by undergoing reverse intersystem crossing in response to an application of energy. The chromophores may then return to a ground state and emit light through fluorescence. As a result, the chromophores of the present disclosure may be suitable for use in applications, such as in organic light-emitting diodes, that utilize the light emitted from the chromophores in response to an application of electrical energy. Accordingly, the present disclosure is also directed to organic layers, such as polymers or films, which comprise the chromophores.

As described previously in the present disclosure, the chromophore may comprise a donor ligand. As used in the present disclosure, the term "donor ligand" may refer to an organic ligand capable of forming a charge-transfer complex or an electron-donor-acceptor complex with an acceptor ligand, described subsequently in the present specification, capable of transferring at least one electron from the donor ligand to the acceptor ligand upon excitation. In embodiments, the donor ligand may comprise an aromatic amine, a nitrogen heterocycle, or combinations of these. For example, the donor ligand may comprise carbazole (CBZ), diphenylamine (DPA), phenothiazine (PTZ), phenoxazine (POZ), acridine (ACN), or combinations of these.

In embodiments, the donor ligand may be partially substituted. For example, the donor ligand may be partially substituted as follows:

(CBZ)

wherein each of $R_2$ and $R_3$ are selected from one or more of hydrogen, an alkyl group, t-butyl, a methoxy group, fluorine, chlorine, bromine, nitrile, a trifluoromethyl group, a trimethylsilyl group, or combinations of these;

(DPA)

wherein each of $R_2$ and $R_3$ are selected from one or more of hydrogen, an alkyl group, t-butyl, a methoxy group, fluorine, chlorine, bromine, nitrile, a trifluoromethyl group, a trimethylsilyl group, or combinations of these;

(PTZ)

wherein each of $R_2$ and $R_3$ are selected from one or more of hydrogen, an alkyl group, t-butyl, a methoxy group, fluorine, chlorine, bromine, nitrile, a trifluoromethyl group, a trimethylsilyl group, or combinations of these;

(POZ)

wherein each of $R_2$ and $R_3$ are selected from one or more of hydrogen, an alkyl group, t-butyl, a methoxy group, fluorine, chlorine, bromine, nitrile, a trifluoromethyl group, a trimethylsilyl group, or combinations of these; and

(ACN)

wherein each of $R_2$ and $R_3$ are selected from one or more of hydrogen, an alkyl group, t-butyl, a methoxy group, fluorine, chlorine, bromine, nitrile, a trifluoromethyl group, a trimethylsilyl group, or combinations of these.

As described previously in the present disclosure, the chromophore may comprise an acceptor ligand. As used in the present disclosure, the term "acceptor ligand" may refer to an organic ligand capable of forming a charge-transfer complex or an electron-donor-acceptor complex with the donor ligand, described previously in the present specification, capable of transferring at least one electron from the donor ligand to the acceptor ligand upon excitation. In embodiments, the acceptor ligand may comprise a nitrogen heterocycle, such as an oxazole or a thiazole, an organosulfur compound, or combinations of these. For example, the acceptor ligand may comprise benzoxazole (BOX), benzothiazole (BTZ), diphenyl sulfone (DPS), or combinations of these.

As described previously in the present disclosure, the chromophore may comprise an acceptor tuner ligand. Without being bound by any particular theory, it is believed that the acceptor tuner ligand may allow for the covalent incorporation of the chromophore into an organic layer, such as poly(arylene ether)s (PAE). In particular, PAE is typically produced by a nucleophilic aromatic substitution, which generally requires a nucleophilic component and an electrophilic component. Accordingly, the acceptor tuner ligand may be selected such that the chromophore may function as either the nucleophilic component or the electrophilic component, depending on the requirements of the particular PAE the chromophore will be incorporated into. In embodiments, the acceptor tuner ligand may comprise benzene. In embodiments, the acceptor tuner ligand may comprise a partially substituted or fully substituted benzene ring. For example, the acceptor tuner ligand may comprise a substituted benzene ring as follows:

(BNZ)

wherein X is selected from one or more of $R_1$, hydrogen, or combinations of these. In embodiments, the benzene ring is substituted with at least two $R_1$ groups. In embodiments, the benzene ring may be substituted with two $R_1$ groups located at the 2 and 3 position of the benzene ring, the 2 and 4 position of the benzene ring, the 2 and 5 position of the benzene ring, or the 2 and 6 position of the benzene ring. For example, the acceptor tuner ligand may comprise a 2,3-substituted benzene, a 2,4-substituted benzene, a 2,5-substituted benzene, or a 2,6-substituted benzene, wherein the substituted groups comprise one or more $R_1$ group. In embodiments, $R_1$ may be selected from one or more of fluorine, chlorine, bromine, hydroxyl, thiol, nitro, nitrile, trifluoromethyl, amine, alkyl, ester, sulfonyl, sulfonamide, acyl, amide, ether, aryl, trialyklsilyl, trialkylsiloxy, or combinations of these. For example, the acceptor tuner ligand may comprise 3,5-difluorophenyl, 2,4-difluorophenyl, 3,5-dihydroxyphenyl, 2,4-dihydroxyphenyl, or combinations of these.

In production, various techniques may be used to synthesize the chromophore. In embodiments, an intermediate is first synthesized by the coupling, such as through nucleophilic substitution, of an acceptor ligand and an acceptor tuner ligand. The chromophore may then be synthesized by the coupling of the intermediate and a donor ligand. For example, a chromophore comprising a donor ligand, an acceptor ligand comprising diphenyl sulfone, and an acceptor tuner ligand, may have a general structure as follows:

(CRM1)

wherein ($Ar_1$) represents the acceptor tuner ligand and ($Ar_2$) represents the donor ligand. Similarly, a chromophore comprising a donor ligand, an acceptor ligand comprising benzoxazole, and an acceptor tuner ligand, may have a general structure as follows:

(CRM2)

wherein ($Ar_1$) represents the acceptor tuner ligand and ($Ar_2$) represents the donor ligand. Similarly, a chromophore comprising a donor ligand, an acceptor ligand comprising benzothiazole, and an acceptor tuner ligand, may have a general structure as follows:

(CRM3)

wherein ($Ar_1$) represents the acceptor tuner ligand and ($Ar_2$) represents the donor ligand.

As noted previously in the present disclosure, these chromophores may be capable of thermally activated delayed fluorescence. That is, these chromophores may be capable of transitioning from a triplet state to a singlet state by undergoing reverse intersystem crossing in response to an application of energy. The chromophores may then return to a ground state and emit light through fluorescence. In particular, the chromophores of the present disclosure may emit blue light when undergoing thermally activated delayed fluorescence. That is, the light emitted by the chromophores of the present disclosure during thermally activated delayed fluorescence may have a wavelength of from 450 nanometers (nm) to 485 nm. Additionally, the chromophores of the present disclosure may be capable of emitting blue light at a quantum efficiency greater than 15%. For example, the chromophores of the present disclosure may be capable of emitting blue light at a quantum efficiency greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or even greater than 99%.

Accordingly, the chromophores of the present disclosure may be suitable for use in a number of applications, such as in an organic light emitting diode. In embodiments, the chromophores may be incorporated in an organic layer suitable for applications such as organic light emitting diodes. In embodiments, the chromophores may be incorporated into a film or polymer material. These organic layers may then be incorporated into the organic light-emitting diodes as the emissive electroluminescent layer, which emits light, particularly blue light, in response to an electric current applied by the electrodes of the organic light-emitting diodes.

As described previously in the present disclosure, the chromophores may be incorporated into an organic layer, such as a polymer or a film. In embodiments, the chromophores may be incorporated into a suitable electroluminescent conductive polymer. In embodiments, the chromophores may be covalently incorporated into a PAE material. In embodiments, the PAE material may comprise a homopolymer. As used in the present disclosure, the term "homopolymer" may refer to a polymeric compound comprising one or more of the presently disclosed chromophores and prepared by the polymerization of a single monomer. In embodiments, the PAE material may comprise a copolymer. As used in the present disclosure, the term "copolymer" may refer to a polymeric compound comprising one or more of the presently disclosed chromophores and prepared by the polymerization of two or more different comonomers. Without being bound by any particular theory, it is believed that the incorporation of the chromophores into a PAE material may result in increased thermo-oxidative stability when compared to polymers that may be used in conventional organic light emitting diodes. That is, the PAE material may resist thermal and oxidative degradation at conventional operating temperatures of organic light emitting diodes and, as a result, may improve the durability and stability of organic light emitting diodes.

As described previously in the present disclosure, it is believed that the acceptor tuner ligand may allow for the covalent incorporation of the chromophore into the PAE material. That is, in embodiments, the chromophore may be selected based on the functional groups of the acceptor tuner ligand in order to effectively incorporate the chromophore into the PAE material. Accordingly, in embodiments where the acceptor tuner ligand comprises a benzene ring substituted with fluorine or chlorine (i.e., where $R_1$ is selected from fluorine or chlorine), the PAE material may comprise the general formula:

$$\{[M_1]_x\text{-}[M_2]_{1-x}\text{-}M_3\}_n \quad \text{(PAE1)}$$

wherein $M_1$ is a chromophore of the present disclosure, $M_2$ is a first comonomer, and $M_3$ is a second comonomer. In embodiments where the acceptor tuner ligand comprises a benzene ring substituted with a hydroxyl group or a thiol group (i.e., where $R_1$ is selected from a hydroxyl group or a thiol group), the PAE material may comprise the general formula:

$$\{[M_1]_x\text{-}[M_3]_{1-x}\text{-}M_2\}_n \quad \text{(PAE2)}$$

wherein $M_1$ is a chromophore of the present disclosure, $M_3$ is a first comonomer, and $M_2$ is a second comonomer. In embodiments, $M_2$ and $M_3$ may each be selected from 4,4'-difluorodiphenyl sulfone, 4,4'-difluorobenzophenone, 4,4'-difluorotriphenylphosphine oxide, 2,5-bis(4-fluorophenyl)-1,3,4-oxadiazole, 2,3-bis(4-fluorophenyl)-quinoxaline, 2,5-bis(4-fluorophenyl)-oxazole, bisphenol-A, bisphenol-AF, 4,4'-dihydroxybiphenyl, 4,4'-dihydroxydiphenyl ether, hydroquinone, catchol, resorcinol, or combinations of these. For example, in embodiments $M_2$ may be selected from one or more of 4,4'-difluorodiphenyl sulfone, 4,4'-difluorobenzophenone, 4,4'-difluorotriphenylphosphine oxide, 2,5-bis(4-fluorophenyl)-1,3,4-oxadiazole, 2,3-bis(4-fluorophenyl)-quinoxaline, 2,5-bis(4-fluorophenyl)-oxazole, or combinations of these, and $M_3$ may be selected from one or more of bisphenol-A, bisphenol-AF, 4,4'-dihydroxybiphenyl, 4,4'-dihydroxydiphenyl ether, hydroquinone, catechol, resorcinol, or combinations of these.

For example, a PAE material that comprises the general formula of PAE1 may have a general structure as follows:

wherein $M_1$ comprises a chromophore of the present disclosure, $M_2$ comprises 4,4'-difluorodiphenyl sulfone, and $M_3$ comprises bisphenol-A. Similarly, a PAE material that comprises the general formula of PAE2 may have a general structure as follows:

wherein $M_1$ comprises a chromophore of the present disclosure, $M_2$ comprises 4,4'-difluorodiphenyl sulfone, and $M_3$ comprises bisphenol-A.

Additionally or alternatively, the chromophores of the present disclosure may also be incorporated into one or more film layers. The layers may comprise one or more chromophores or one or more PAE materials comprising one or more chromophores. In embodiments, each layer can be applied to a substrate by any method including, but not limited to, dipping, spraying, pouring, brushing, spin-coating, roller coating, meniscus coating, powder coating, inkjet-type application, controlled-volume application such as drop-on-demand, or combinations of these. For example, in embodiments one or more chromophores may be dissolved in a solvent, such as chloroform, toluene, dichloromethane, 2-methyltetrahydrofuran, or tetrahydrofuran, and the resulting solution may be spin-coated on a substrate. The coated substrate may then be heated to remove excess solvent and produce a film layer comprising one or more chromophores.

EXAMPLES

The various embodiments of thermally activated delayed fluorescence chromophores will be further clarified by the following examples. The examples are illustrative in nature, and should not be understood to limit the subject matter of the present disclosure.

Example 1—Synthesis of 2-(3,5-difluorophenyl) 5-bromobenzoxazole (3,5-DiF-BOX-Br)

A solution was prepared by adding 5.0 grams (g) of 2-amino-4-bromophenol, 5.5 g of 3,5-difluorobenzoic acid, and 50 g of polyphosphoric acid (PPA) to a 250 milliliter (mL) round-bottomed flask equipped with a stir bar and condenser. The flask was immersed in a silicone oil bath and heated to 90 degrees Celsius (° C.) for 12 hours, followed by a second heating to 130° C. for an additional 12 hours. The solution was then slowly poured into 500 mL of vigorously stirred distilled water, which resulted in the precipitation of a solid. The resulting solid was then dissolved in toluene and washed first with distilled water, followed by sodium bicarbonate, followed again with distilled water, and finally brine. The toluene was then dried over magnesium sulfate, filtered, and any remaining solvent was removed via rotary evaporation. The remaining solid material was recrystallized from a solution of ethanol and water, isolated by vacuum filtration, and dried under vacuum to produce 8.16 g (98.0%) of 3,5-DiF-BOX-Br.

Example 2—Synthesis of 3,5-DiF-BOX-CBZ

A solution was prepared by adding 5 g of the 3,5-DiF-BOX-Br prepared in Example 1, 7.0 g of carbazole, 5.0 g of potassium carbonate, copper iodide (10 mol %), N,N-dimethylglycine (20 mol %), and 6 mL of dimethyl sulfoxide to a 250 mL round-bottomed flask equipped with a stir bar and condenser. The flask was then immersed in a silicone oil bath and heated to 80° C. for 52 hours. After being cooled to room temperature, the solution was then slowly poured into 500 mL of vigorously stirred distilled water, which resulted in the precipitation of a solid. The resulting solid was separated by vacuum filtration and dissolved in chloroform. The chloroform solution was washed with distilled water before adding 200 mL of ethanol. The chloroform was then removed from the solution under reduced pressure (~100 torr) and the product, 3,5-DiF-BOX-CBZ, was crystallized. The crystals were isolated by vacuum filtration and the resulting solid was recrystallized from a chloroform-ethanol mixture (1:3) to produce 5.61 g (87%) of 3,5-DiF-BOX-CBz.

Example 3—Synthesis of 2-(3,5-difluorophenyl)-benzothiazole (3,5-DiF-BTZ-I)

First, 2-(3,5-difluorophenyl)-benzothiazole (3,5-DiF-BTZ) was prepared by the reaction of 2-amino thiophenol with 3,5-difluorobenzoic acid in polyphosphoric acid. The 3,5-DiF-BTZ was then iodized adding 2.0 g of the 3,5-DiF-BTZ, 1.96 g of N-iodosuccinimide, and 10 mL of sulfuric acid to a round-bottomed flask. The resulting solution was stirred at room temperature for 24 hours. The solution was then slowly poured into 500 mL of vigorously stirred distilled water, which resulted in the precipitation of a solid that was separated by vacuum filtration. The solid was then dissolved in toluene and washed with a 5% sodium carbonate solution followed by distilled water. The toluene layer was then removed from the solution by a separatory funnel, dried over magnesium sulfate, and evaporated in a rotary evaporator. The remaining solid was dissolved in chloroform and washed, by vigorously stirring, with a solution of 10% sodium bisulfite. The organic layer was washed with distilled water and brine, dried over magnesium sulfate, and evaporated to dryness via a rotary evaporator. The resulting solid was recrystallized from a mixture of chloroform, ethanol and toluene (1:1:8) to produce 1.53 g (52%) of 3,5-DiF-BTZ-I.

Example 4—Synthesis of 3,5-DiF-BTZ-CBZ

A solution was prepared by adding 0.5 g of the 3,5-DiF-BTZ-I prepared in Example 3, 0.7 g of carbazole, 0.5 g of potassium carbonate, copper iodide (10 mol %), N,N-dimethylglycine (20 mol %), and 3 mL of dimethyl sulfoxide to a 10 mL round-bottomed flask equipped with a stir bar and condenser. The flask was then immersed in a silicone oil bath and heated to 80° C. for 24 hours. After being cooled to room temperature, the solution was then slowly poured into 500 mL of vigorously stirred distilled water, which resulted in the precipitation of a solid. The resulting solid was separated by vacuum filtration and dissolved in 150 mL of chloroform. The chloroform solution was then washed with distilled water before adding 100 mL of ethanol. The chloroform was then removed from the solution under reduced pressure (~100 torr) and the product, 3,5-DiF-BTZ-CBZ, was crystallized. The crystals were isolated by vacuum filtration and the resulting solid was recrystallized from a chloroform-ethanol mixture (4:1) to produce 0.4 g (78%) of 3,5-DiF-BTZ-CBz.

Example 5—Fluorescence of Chromophore Films Under Air Gas

First, a solution was prepared by dissolving 3,5-DiF-BTZ-CBZ in chloroform such that the concentration of 3,5-DiF-BTZ-CBZ was 3 milligram per milliliter (mg/mL). Next, 0.2 mL of the solution was spin-coated on cleaned quartz substrates at 500 rotations per minute (rpm) for 1 minute. The coated substrates were then heated in an oven at 110° C. for 10 minutes. The samples were then placed in a fluorimeter chamber under a constant flow of air gas and subjected to a 320 nm excitation. An emission spectrum was then measured every half hour for two hours. The results are depicted in FIGS. 1A and 1B.

Figure 1A:
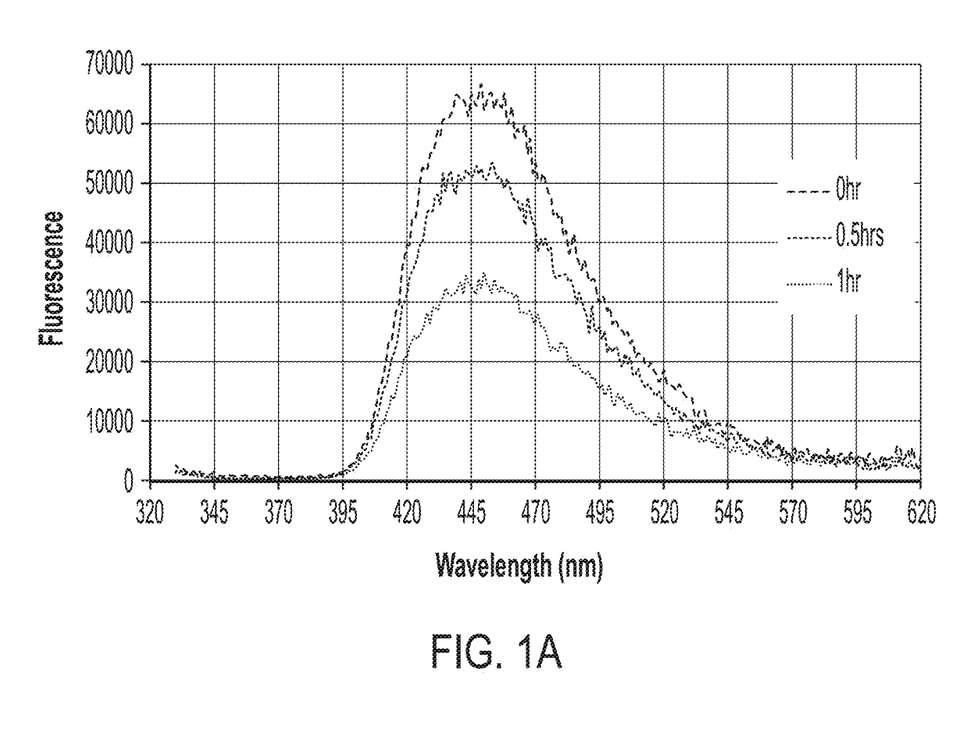
FIG. 1A graphically depicts the emission profiles of a film comprising a chromophore, according to one or more embodiments of the present disclosure.
Figure 1B:
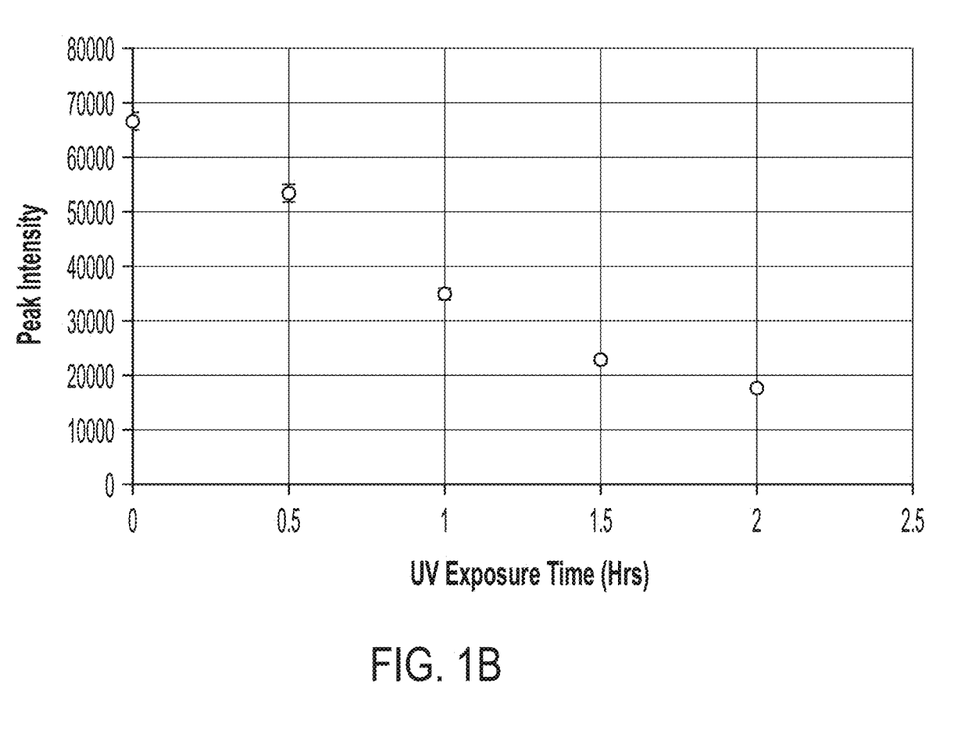
FIG. 1B graphically depicts the emission peak intensity (y-axis) of the film of FIG. 1 as a function of time inside a fluorimeter chamber (x-axis), according to one or more embodiments of the present disclosure.

As shown in FIG. 1A, the 3,5-DiF-BTZ-CBZ film exhibits an emission that peaks within the blue range of the visible light spectrum. However, as shown by FIGS. 1A and 1B, the intensity of the emission decreased as the time spent under excitation increased. Without being bound by any particular theory, it is believed that this may suggest that the chromophores in a triplet state may be quenched by oxygen present in the air gas. As such, the number of chromophores undergoing thermally activated delayed fluorescence may be decreased and, as a result, the intensity of the emissions is also decreased.

Example 6—Fluorescence of Chromophore Films Under $N_2$ Gas

First, a solution was prepared by dissolving 3,5-DiF-BTZ-CBZ in chloroform such that the concentration of 3,5-DiF-BTZ-CBZ was 3 milligram per milliliter (mg/mL). Next, 0.2 mL of the solution was spin-coated on cleaned quartz substrates at 500 rotations per minute (rpm) for 1 minute. The coated substrates were then heated in an oven at 110° C. for 10 minutes. The samples were then placed in a fluorimeter chamber under a constant flow of nitrogen gas and subjected to a 320 nm excitation. An emission spectrum was then measured every hour for five hours. The results are depicted in FIGS. 2A and 2B.

Figure 2A:
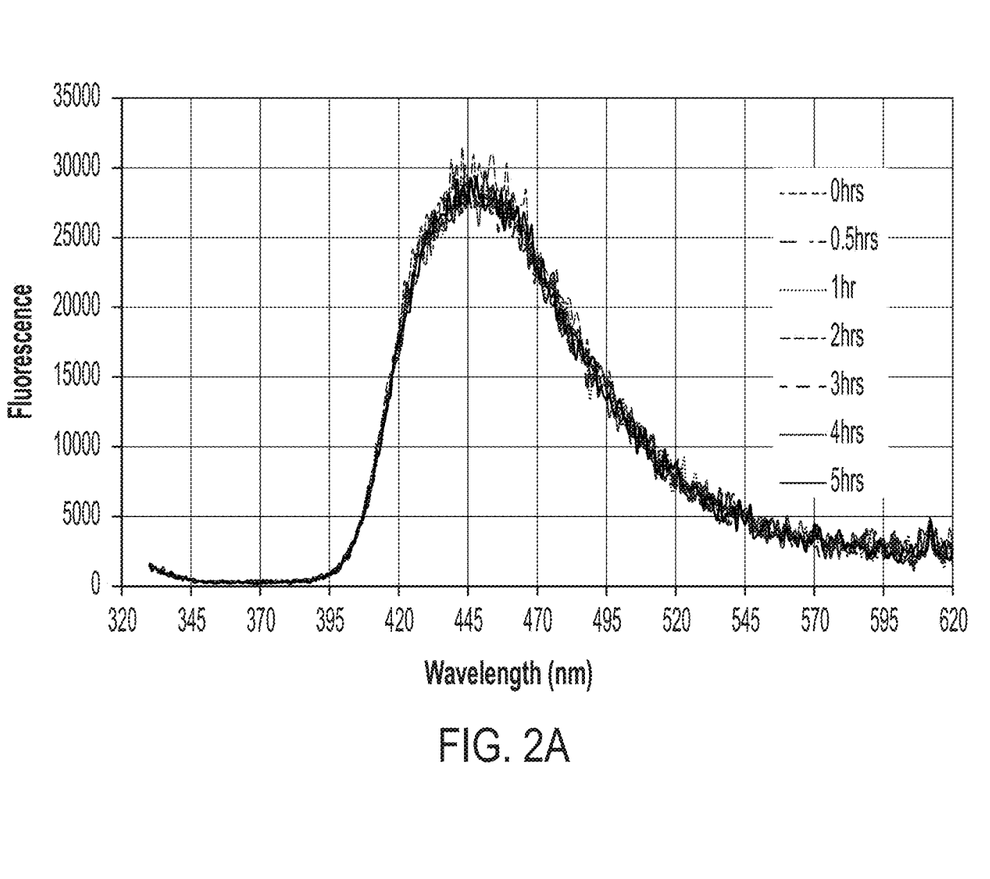
FIG. 2A graphically depicts the emission profiles of a film comprising a chromophore, according to one or more embodiments of the present disclosure.
Figure 2B:
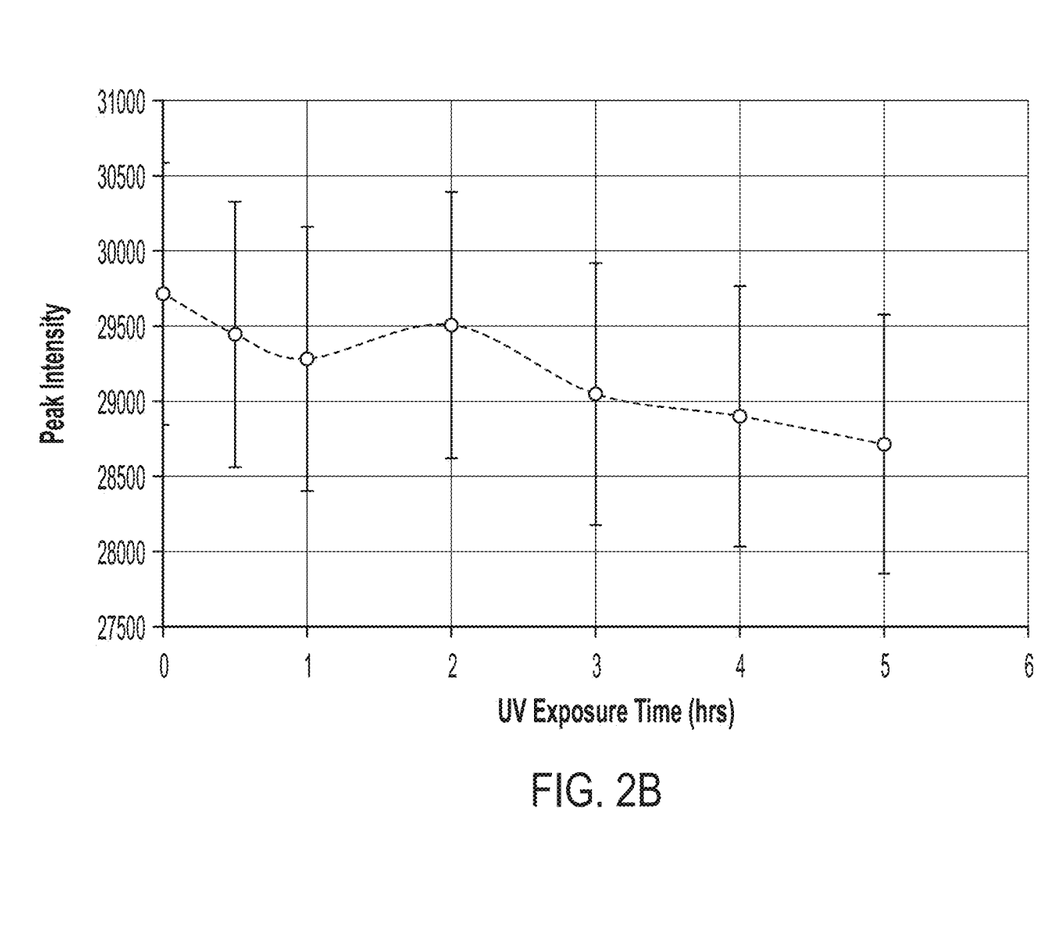
FIG. 2B graphically depicts the emission peak intensity (y-axis) of the film of FIG. 2 as a function of time inside a fluorimeter chamber (x-axis), according to one or more embodiments of the present disclosure.

As shown in FIG. 2A, the 3,5-DiF-BTZ-CBZ film exhibits an emission that peaks within the blue range of the visible light spectrum. Additionally, in contrast to samples of Example 5, the intensity of the emissions remained fairly constant over the duration of 5 hours, as shown by FIGS. 2A and 2B. As the constant flow of nitrogen gas removed any oxygen present in the fluorimeter chamber, this stability may be due, at least in part, to the prevention of the quenching of chromophores in a triplet state. Additionally, this constant intensity may indicate that the chromophores are extremely stable, even at a high excitation levels. This may further indicate that the chromophores are suitable for use in harsher operating conditions without suffering degradation and negatively affecting the durability of the device they are incorporated in.

It will be apparent to those skilled in the art that various modifications and variations can be made without departing from the spirit or scope of the disclosure. Since modifications, combinations, sub-combinations and variations of the disclosed embodiments incorporating the spirit and substance of the disclosure may occur to persons skilled in the art, the scope of the disclosure should be construed to include everything within the scope of the appended claims and their equivalents.

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments, it is noted that the various details described in this disclosure should not be taken to imply that these details relate to elements that are essential components of the various embodiments described in this disclosure. Rather, the appended claims should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A thermally activated delayed fluorescence chromophore of the general structure:

wherein $Ar_1$ represents an acceptor tuner ligand and $Ar_2$ represents a donor ligand, wherein the acceptor tuner ligand is a benzene ring at least partially substituted with two or more fluoro atoms and wherein the donor ligand is an optionally substituted carbazole.

2. The thermally activated delayed fluorescence chromophore of claim 1, wherein the donor ligand is partially substituted carbazole with the structure:

wherein each of $R_2$ and $R_3$ are independently selected from an alkyl group, a methoxy group, fluorine, chlorine, bromine, nitrile, a trifluoromethyl group, or a trimethylsilyl group.

3. The thermally activated delayed fluorescence chromophore of claim 1, wherein the two of the two or more fluoro atoms of the benzene ring are located at the 2 and 3 position of the benzene ring, the 2 and 4 position of the benzene ring, the 2 and 5 position of the benzene ring, or the 2 and 6 position of the benzene ring.

4. The thermally activated delayed fluorescence chromophore of claim 1, wherein the acceptor tuner ligan is 3,5-difluorinated benzene.

* * * * *